United States Patent [19]

Shinmoto et al.

[11] Patent Number: 5,573,937
[45] Date of Patent: Nov. 12, 1996

[54] SERUM FREE CULTURE MEDIUM

[75] Inventors: Hiroshi Shinmoto; Shun-ichi Dousako, both of Saitama-ken, Japan

[73] Assignee: Snow Brand Milk Products Co., Ltd., Hokkaido, Japan

[21] Appl. No.: 370,218

[22] Filed: Jan. 9, 1995

Related U.S. Application Data

[63] Continuation of Ser. No. 759,424, Sep. 13, 1991, abandoned, which is a continuation-in-part of Ser. No. 616,903, Nov. 21, 1990, abandoned.

[30] Foreign Application Priority Data

Dec. 7, 1989 [JP] Japan ..................................... 1-318439

[51] Int. Cl.$^6$ .............................. C12N 5/12; C12N 5/02; C12N 5/00
[52] U.S. Cl. ..................................... 435/240.1; 435/240.2; 435/240.3; 435/240.31; 435/240.26; 435/240.27; 935/89
[58] Field of Search .............................. 435/240.1, 240.2, 435/240.3, 240.31, 240.26, 240.27; 935/89

[56] References Cited

U.S. PATENT DOCUMENTS

| | | | |
|---|---|---|---|
| 4,668,771 | 5/1987 | Kawakami et al. | 530/366 |
| 4,851,346 | 7/1989 | Chan | 435/240.31 |
| 5,019,499 | 5/1991 | Murakami | 435/69.1 |

OTHER PUBLICATIONS

Kovar et al Biotechnology Letters vol. 9, No. 4 pp. 259–264 (1987).

*Primary Examiner*—Esther Kepplinger
*Assistant Examiner*—Choon P. Koh
*Attorney, Agent, or Firm*—Burgess, Ryan and Wayne

[57] ABSTRACT

A novel serum-free culture medium is provided which contains inorganic iron compound as a growth factor for the culture of animal cells. Culture products are easy to purify from the culture broth.

8 Claims, 5 Drawing Sheets

SERUM FREE CULTURE MEDIUM

RELATED APPLICATION

This application is a continuation of application Ser. No. 07/759,424, filed Sep. 13, 1991, now abandoned, which is a continuation-in-part of U.S. application Ser. No. 616,903, filed Nov. 21, 1990, now abandoned, the entire contents of which is incorporated herein by reference.

BACKGROUND OF THE INVENTION

1. Field of the Invention

The present invention relates to a serum-free culture medium used for the culture of animal cells.

2. Description of the Prior Art

In producing materials from animal cells, the selection of the culture medium in which the cells are cultured is very important since the production cost depends upon the price of the culture medium as well as the purifying costs of the final products.

Previously, a culture medium has been used containing about 10% of animal sera added to the basal synthetic culture medium for culturing animal cells.

However, the addition of sera increased the cost of the culture medium. Not only that, but the purifying cost of the product was likewise raised by the enriched protein contained in the sera.

Thus, a serum-free culture medium has been developed containing no sera. The serum-free culture medium is in general use at present for producing various materials. It is also known that various cell growth supplements can be added to a serum free culture medium. Representative examples are insulin, ethanol amine, sodium selenite, transferrin, albumin, lipoprotein, cytokine, and the like. Those which may raise the cost of the culture medium and the purifying cost of products include protein growth supplements. It is, therefore, indispensable to develop a serum-free culture medium containing little or essentially no protein.

The one which is comparatively expensive is transferrin among the growth supplements which are added to the serum-free culture medium.

Transferrin is considered to function as a growth supplement which is efficient in supplying cells with iron ions. (Newest Medical Science, Vol. 40, Growth Promotion by Transferrin" by Kimura and Ozawa, pages 554–559, 1985, and "Cell Growth Factor", pages 152–155, compiled by Japan Association of Tissue Culture Science, 1980).

The following recycling model of transferrin is asserted by Kogo, et al.

Iron-saturated transferrin is taken into cells by receptor-mediated endocytosis. After iron ions are released within the cells, transferrin is again secreted outside of the cells. ("Anemia by Iron Membrane Permeability Troubles" by Niitsu and Kogo, Separate Volume 3, Course of Medical Science, Medical Topics, page 124, 1988).

The above suggests that transferrin continues to supply cells with iron ions repeatedly.

On the contrary, Mather and Sato have reported that, in the serum-free culture medium containing F12 as its basal synthetic culture medium, the growth promotion by transferrin was replaced by highly concentrated iron ions. (J. P. Mather and G. H. Sato, Experiment Cell Research, Vol. 120, pages 191–200, 1979).

Further, Kovar and Franek report that, in the serum-free culture medium for mouse hybridoma composed of RPMI 1640 as the basal synthetic culture medium, the addition of a high concentration (500 μM) of ferric citrate makes it possible to culture the hybridoma in non-protein serum-free culture. (Biotechnology Letters, Vol 9, pages 259–264, 1987).

However, it is known that a high concentration of iron ions is not desirable for cells. A serum-free culture medium should be developed capable of efficiently supplying cells with iron at lower concentrations.

SUMMARY OF THE INVENTION

An object of the present invention is to provide a serum-free culture medium having contained therein an iron compound which may be efficiently utilized by animal cells.

More particularly, an object of the present invention is to provide for a serum-free culture medium having contained therein an iron compound which is comparatively simple in its structure. Further, an object of the present invention is to provide for the serum-free culture medium which is capable of readily purifying cell products. Still further, an object of the present invention is to provide for a serum-free culture medium which would be extensively used for animal cells. Further, an object of the present invention is to provide for a serum-free culture medium which may be economically advantageous and be capable of mass production for industry.

The objects of the present invention have been attained by providing a serum-free culture medium with inorganic iron compound added to the serum-free culture medium as a growth supplement. Namely, the inventors have discovered that the serum-free culture medium with the inorganic iron compound added to the basal synthetic culture medium as the growth supplement was effective in supporting the growth of animal cells, made the purification of their products easier and had extensive uses.

Furthermore, the serum-free culture medium of the present invention may be readily prepared at a lower cost.

The basal synthetic culture medium of the present invention is a culture medium, the principal ingredients of which are an amino acid, inorganic salts, and a saccharide which maintain the basal metabolism of cells. However, it is also possible to provide a serum-free culture medium containing little or essentially no protein which is capable of culturing animal cells, through the combination of the basal synthetic culture medium ERDF (enriched RDF) with inorganic iron compound, for a prolonged period.

When ERDF is used as the basal synthetic culture medium, greater advantages are obtained, compared with other basal synthetic culture medium.

The ERDF is the conventional basal synthetic culture medium for serum-free cultivation. This has been developed by Murakami et al. with an aim at the growth of mouse myeloma NS 1. (Nippon Nogeikagaku Kaishi, pages 575–583, 1984).

The ERDF has the mixture, as the base, of RPMI 1640, Dulbecco's Modified Minimum Essential Medium (DMEM) and Ham's F12 at the ratio of 2:1:1. (This medium shall be called RDF).

The concentration of amino acid is tripled and that of glucose doubled. The concentration of vitamins is also increased. Further, the osmotic pressure of the culture medium is adjusted at 290 mOsm, 5% higher than that of the normal culture medium.

The composition thereof is shown in Table 1.

TABLE 1

| Composition ERDF | | Composition ERDF | |
| --- | --- | --- | --- |
| NaCl | 110.0 mM | Tryptophan | 0.09 |
| KCl | 5.0 | Tyrosine | 0.48 |
| $MgSO_4$ | 0.55 | Valine | 0.93 |
| — | — | p-Amino benzoic acid | $3.7 \times 10^{-3}$ |
| $CaCl_2.2H_2O$ | 0.74 | Biotin | $4.1 \times 10^{-4}$ |
| — | — | Pantothenate.Ca | $2.6 \times 10^{-3}$ |
| $Na_2HPO_4.12H_2O$ | 3.41 | Cholin chloride | $8.8 \times 10^{-2}$ |
| $CuSO_4.5H_2O$ | $3.0 \times 10^{-6}$ | Folic acid | $4.1 \times 10^{-3}$ |
| | $8.0 \times 10^{-4}$ | Inositol | $2.6 \times 10^{-1}$ |
| $Fe(NO_3)_3.9H_2O$ | — | Niacinamide | $1.2 \times 10^{-2}$ |
| $ZnSO^4.7H_2O$ | $8.0 \times 10^{-4}$ | Pyridoxal.HCl | $4.9 \times 10^{-3}$ |
| | | Pyridoxine.HCl | $2.5 \times 10^{-3}$ |
| Alanine | 0.075 | Riboflavine | $5.6 \times 10^{-1}$ |
| Arginine.HCl | 2.76 | Thiamin.HCl | $4.7 \times 10^{-3}$ |
| Asparagine.$H_2O$ | 0.63 | Vitamin $B_{12}$ | $2.5 \times 10$ |
| Aspartic Acid | 0.30 | Lipoic Acid | $2.5 \times 10^{-4}$ |
| Cysteine.HCl.$H_2O$ | 0.60 | Glutathione | $1.6 \times 10^{-3}$ |
| Glutamic acid | 0.27 | Glucose | 19.00 |
| Glutamine | 6.84 | Hypoxanthine | $7.5 \times 10^{-3}$ |
| Glycine | 0.57 | Putrescine.$2H_2O$ | $2.5 \times 10^{-4}$ |
| Histidine.HCl.$H_2O$ | 0.36 | Pyruvate.Na | 1.0 |
| Hydroxyproline | 0.24 | Thymidine | $7.5 \times 10^{-3}$ |
| Isoleucine | 1.20 | Linoleic acid | $7.5 \times 10^{-5}$ |
| Leucine | 1.26 | | |
| Lysine.HCl | 1.08 | Phenol red | 5.0 mg/l |
| Methionine | 0.33 | HEPES | 1.19 g/l |
| Phenylalanine | 0.45 | $NaHCO_3$ | 12.50 mM |
| Proline | 0.48 | Streptomycin | 0.1 g/l |
| Serine | 0.81 | Penicillin | $10^5$ U/l |
| Threonine | 0.93 | | |

The requirements for the ERDF of the present invention are not as strict as those described above. As long as the object and effect thereof are satisfied, it is permitted to make deletions, additions or alterations of a part of the ingredients or the alteration of the amounts used.

Further, when insulin (I), transferrin (T), ethanol amine (E) and selenium (S) are added to the ERDF, this is called ITES-ERDF. This culture medium is extensively used for culturing mouse hybridoma or human hybridoma. But the ITES-ERDF is not used for the present invention, because its protein concentration is high (25 μg/ml).

0.8 μM of iron sulfide $FeSO_4$ is included in the ERDF.

The iron concentration is the same as that of the mixed culture medium, RPMI 1640: DMEM: F12=2:1:1, which is the original prescription of ERDF. it is not optimized.

The serum-free culture medium of the present invention has ERDF as its basal synthetic culture medium. Further, the concentration of inorganic iron was increased within the culture medium. The preferred one is the IES-ERDF having enriched concentration of inorganic iron to about 40–100μM per liter of the culture medium or the ES-ERDF having enriched the concentration of the inorganic iron to about 40–80 μM. The protein concentration in this culture medium may be preferably reduced to about 5 mg or less protein per liter of the basal culture medium, or essentially no protein. If such procedure is followed, the protein concentration is lowered and it becomes easier to purify cell products.

For lowering the protein content, it may be advisable to keep insulin, for example, at about 5 μg/ml (IES-ERDF) having enriched the inorganic iron concentration up to 40–100 μM) in the culture medium.

In case of the protein free culture medium, it may be advisable to use, for example, the ES-ERDF having enriched inorganic it;on concentration up to about 40–80 μM.

Even if such culture medium is Used, it is possible to carry out the continuous cultivation of such animal cells as hybridoma, etc. for the prolonged period.

Further, there is no difference With ITES-ERDF in antibody production.

The cells which can be cultured in the ITES-ERDF are capable of continuous culture in the inorganic iron—enriched IES-ERDF and inorganic iron—enriched ES-ERDF. Thus, this inorganic iron—enriched serum-free culture medium is suitable for the culture of mouse hybridoma derived from such parental Stocks as SP2 or X63.

Those compounds which may be used as inorganic iron are ferrous sulfate, ferrous chloride, ferric nitrate thereof.

The present invention provides a novel serum-free culture medium having inorganic iron compound added as a growth supplement to the basal culture medium. By using the culture medium of the present invention, it is possible to culture animal cells as efficiently as when serum-containing culture medium is used. Further, it is easier to purify products than when the serum culture medium is used.

The present invention is particularly useful when ERDF is used as the basal synthetic culture medium.

Abbreviations relating to the culture medium of the present invention are defined as follows.

"I" represents insulin; "T", transferrin; "E", ethanol amine; and "S", sodium selenite.

The designation put before ERDF shows that such and such ingredients are contained (for example, ES-ERDF= ERDF containing ethanol amine and selenium.

Further, "R" of the culture medium RDF shows "RPMI 1640", "D" thereof, DMEM; "F", Ham's F12. These show that RDF comprises these culture mediums.

DETAILED DESCRIPTION OF THE INVENTION

The present invention is illustrated by the following examples.

EXAMPLE 1

(1) Cell

In this example, the anti-bovine lactoferrin antibody secreting mouse hybridoma HB8852 was used. (Journal of Dairy Science, Vol. 70, pages 752–759, 1987) This hybridoma was deposited on Apr. 12, 1985, in the American Type Culture Collection, an International Depository Authority, under accession number HB8852.

This hybridoma secretes IgG type antibody. The cells have been subjected to continuous culture in ERDF (Kyokuto Seiyaku) containing 10% Fetal Calf Serum (FCS) (Flow Inc).

A tissue culture flask having 25 cm² of culture area, (Corning 25102S) was used for the successive cultivation of cells.

The cells were cultured in 5% carbon dioxide, 95% air, 90% or higher of humidity, at 37° C.

(2) Serum-Free Culture Medium of Hybridoma

Also used, as the basal synthetic culture medium, was the ERDF (Kyokuto Seiyaku) containing insulin (5 µg/ml, Novo Inc., biphasic insulin), ethanolamine (20 µM, Sigma Inc.) and selenium (sodium selenite, 25 nM, Sigma Inc.) (IES), or ethanolamine and selenium (ES), added thereto.

As iron preparation, there was used ferrous sulfate heptahydrate, ferrous chloride, ferric nitrate nonahydrate (all from Wako Seiyaku).

Before transferring the HB8852 to the serum-free culture medium, hybridoma was precultured in the ERDF (ITES-ERDF) containing insulin, transferrin (10 µg/ml), ethanolamine and selenium for at least one week. Thereafter, the cells were washed three times with the ERDF containing no ITES. This was for avoiding the influence from the FCS used for the successive culture.

(3) Result

A. Hybridoma Growth Promotion Effect by Ferrous Sulfate

Ferrous sulfate was added to the IES-ERDF. The hybridoma was cultured. The concentration of ferrous sulfate originally contained in the ERDF is 0.8 µM. In this experiment, ferrous sulfate was added to the IES-ERDF in the concentration of 5–100 times (4–80 µM) as much as that of the original concentration thereof.

Figure 1:
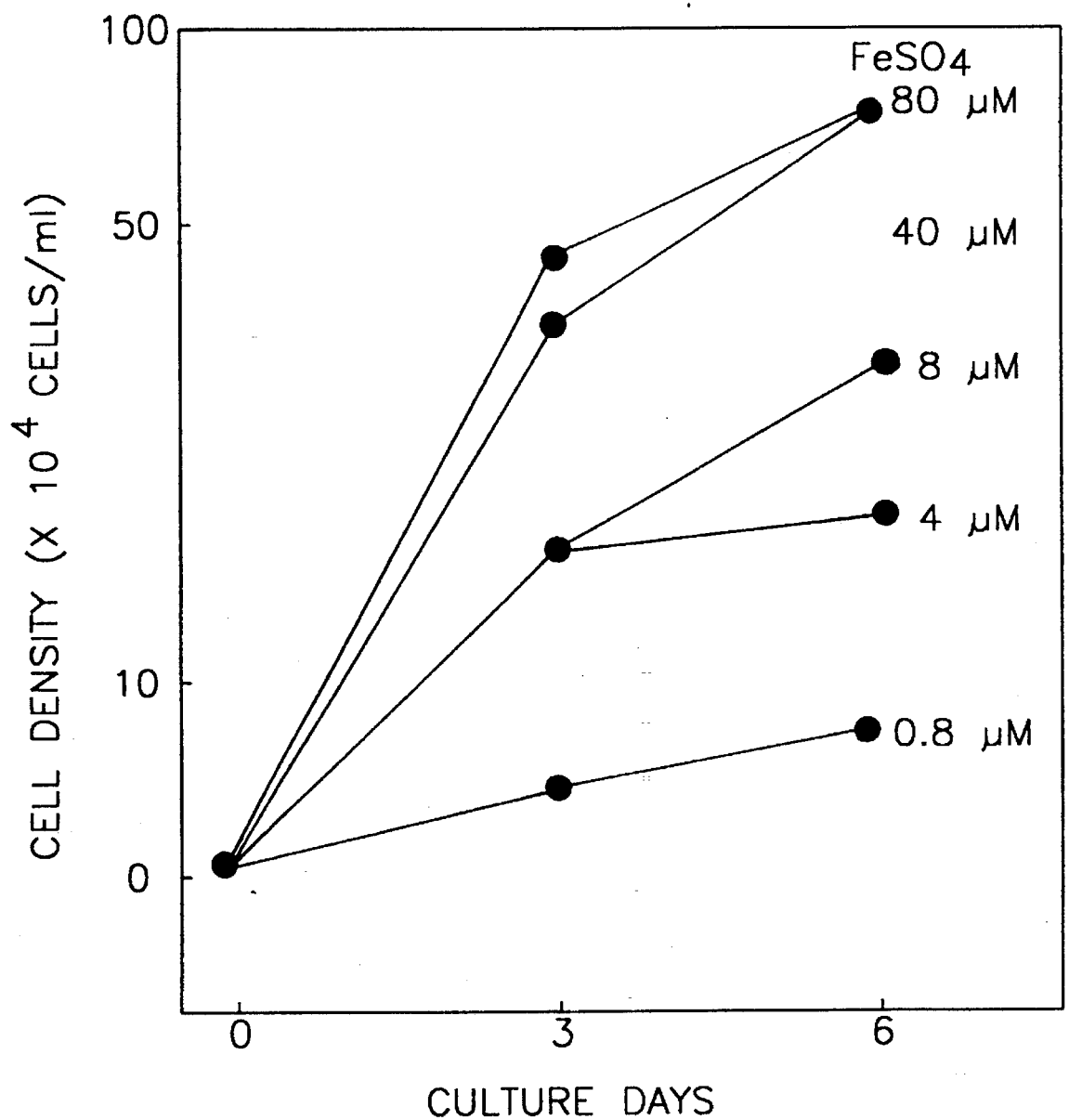
FIG. 1 shows the relationship between the concentration of ferrous sulfate and growth promotion when ferrous sulfate is added to IES-ERDF and hybridoma is cultured.

As shown in FIG. 1, as the volume of ferrous sulfate increases, the growth of the hybridoma is promoted.

In the culture medium in which 40 µM or 80 µM of ferrous sulfate is added, the cell density reached $7.2 \times 10^5$ cell/ml six days after the culture.

B. Hybridoma Growth Promotion by Four Kinds of Inorganic Iron

In order to determine whether the growth of the hybridoma will be influenced by the kind of iron preparations used, hybridoma HB8852 was cultured on the IES-ERDF having therein respectively 80 µM of ferrous sulfate, ferrous chloride, ferric nitrate and potassium ferricyanide $[K_3Fe(CN)_6]$.

Figure 2:
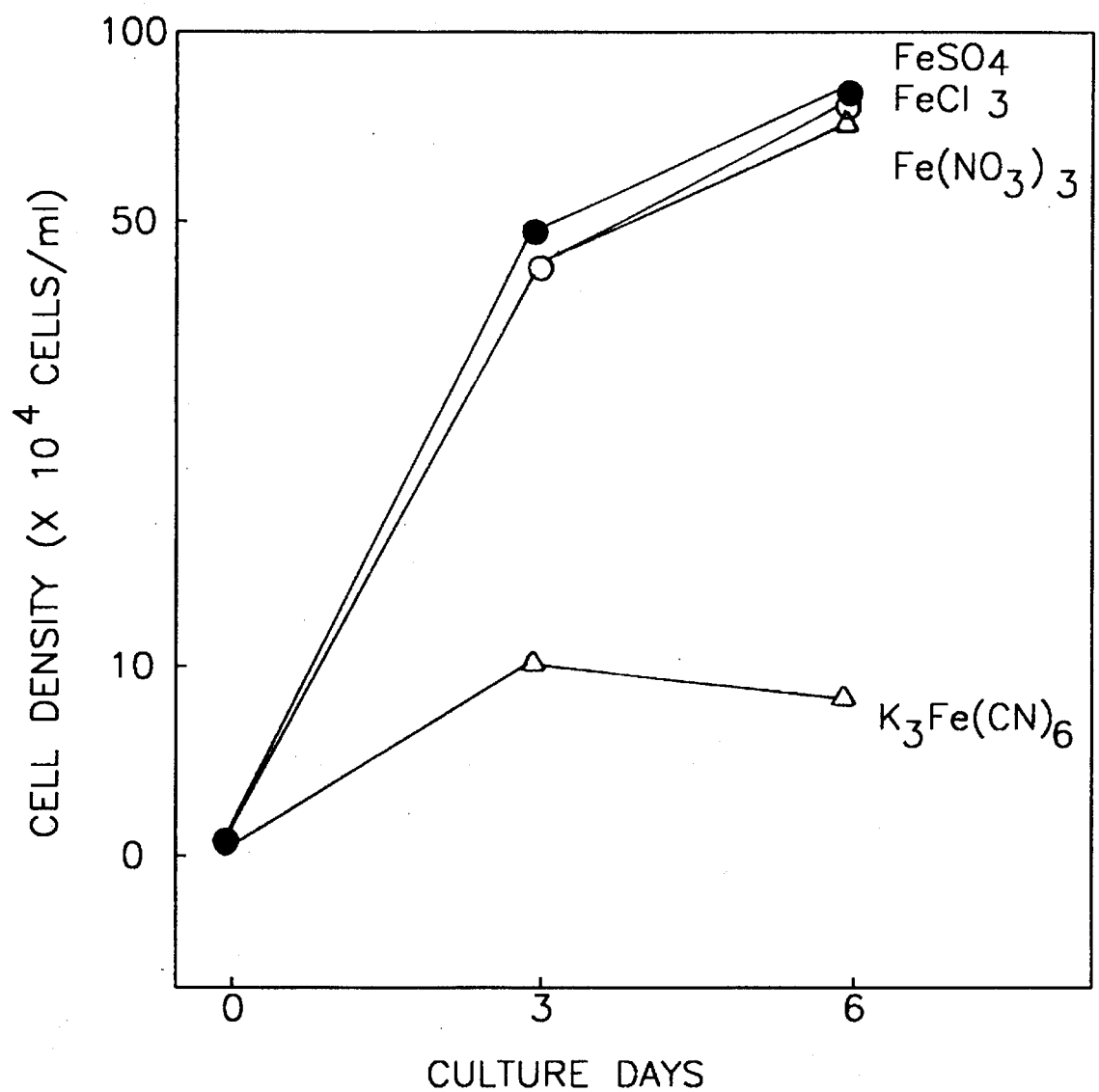
FIG. 2 shows the relationship between the kind of iron salts and growth promotion of hybridoma when it is cultured in the medium having various salts added thereto.

As shown in FIG. 2, the cell density of the hybridoma showed the highest value in the culture medium having therein ferrous sulfate added three days and six days respectively after it was subjected to the culture.

The cell density reached $8.2 \times 10^5$ cells/ml six days thereafter.

Ferrous chloride and iron ferric nitrate showed the same degree of the growth promotion to that of ferrous sulfate. They showed the cell density reached six days thereafter $7.8 \times 10^5$ cells/ml and $7.3 \times 10^5$ cells/ml respectively.

Figure 3:
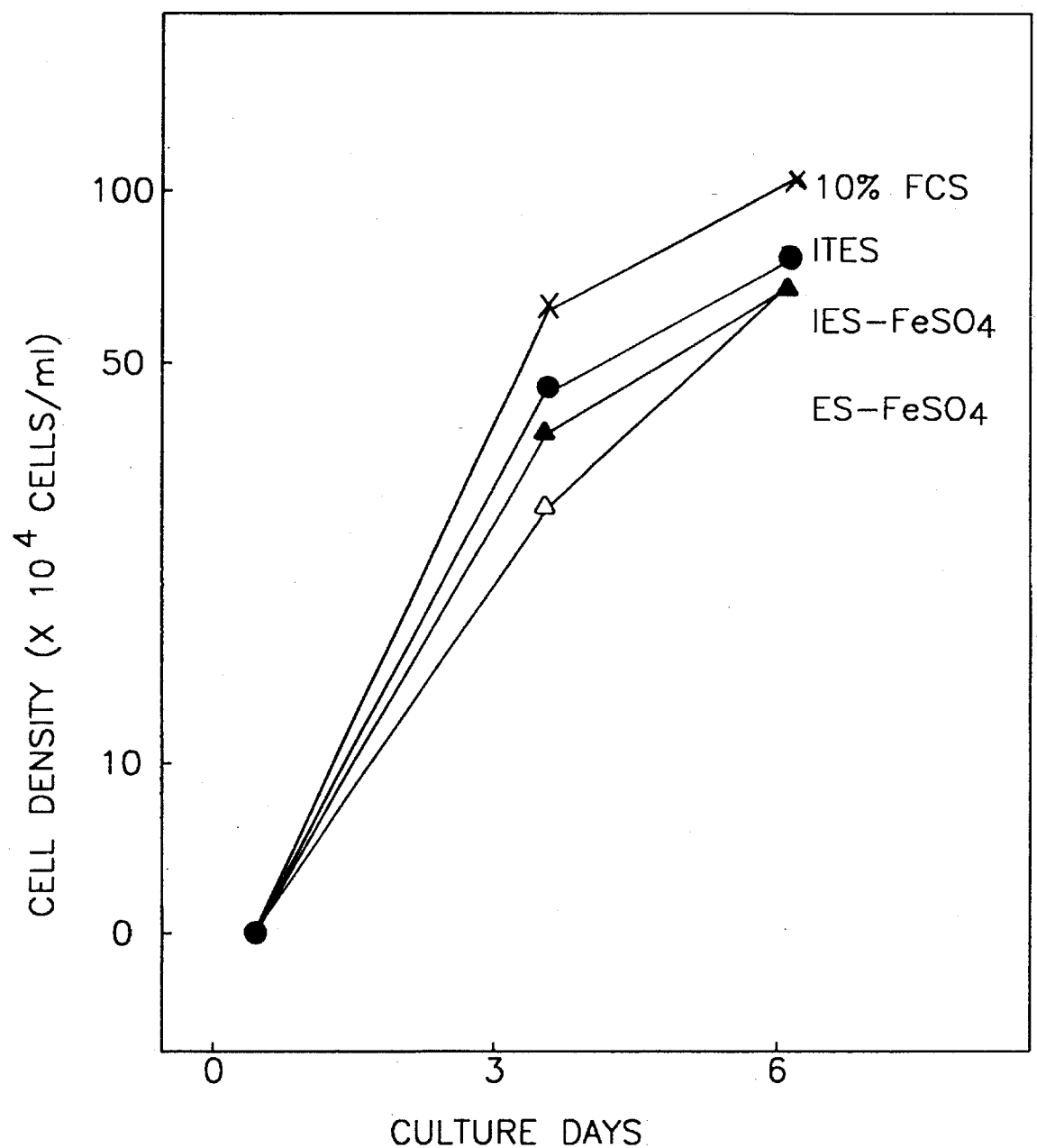
FIG. 3 shows the growth promotion of the hybridoma when it is cultured in the non-protein culture medium with ferrous sulfate added.

C. Hybridoma Growth Promotion in Protein-Free Culture Medium By Ferrous Sulfate 80 uM of ferrous sulfate was added to the ES-ERDF. The hybridoma HB8852 was cultured. As shown in FIG. 3, the excellent growth of the hybridoma was shown even in the essentially protein free culture medium (ES-FeSO₄) containing no insulin.

EXAMPLE 2

(1) Long-Term Cultivation of Hybridoma

The hybridoma was seeded at the density of $1 \times 10^5$ cells/ml, in 10 ml of IES-ERDF or ES-ERDF to which 80 µM of ferrous sulfate was added. The hybridoma was transferred into a tissue culture flask. The cell density was measured every 3–4 days thereafter. It was diluted so as to be about $1 \times 10^5$ cells/ml in the fresh culture medium and subjected to continuous culture for 17 days.

(2) Result

Figure 4:
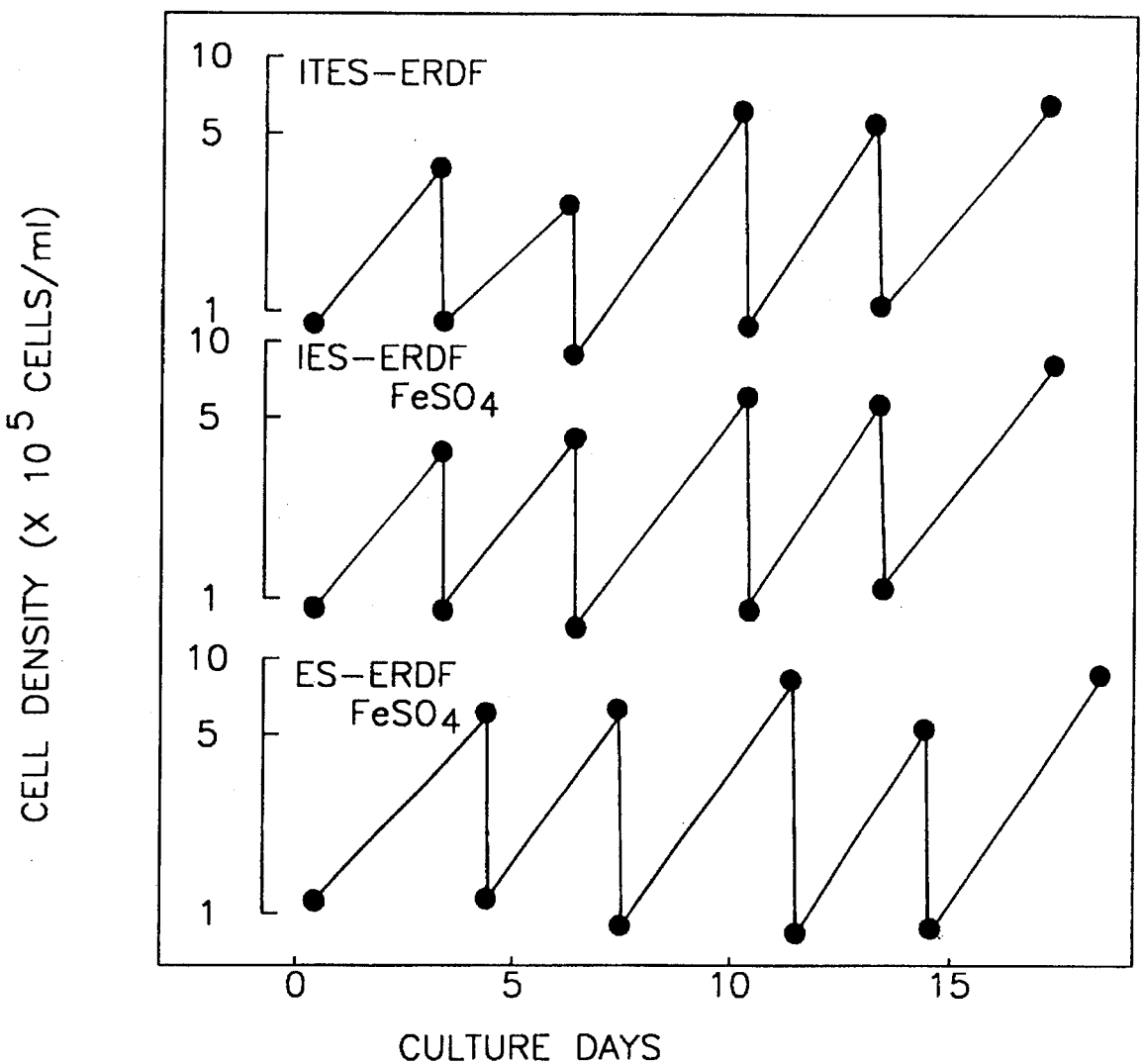
FIG. 4 shows the change in the growth promotion rate when subjected to continuous culture in the medium having ferrous sulfate added thereto.

FIG. 4 shows the result of the long-term culture of the hybridoma HB8852 in the ITES-ERDF or ES-ERDF containing 80 µM of ferrous sulfate.

The growth rate of cells was not reduced during the culture for 17 days.

The mouse hybridoma HB8852 was capable of culturing continuously in the inorganic iron enriched IES-ERDF containing insulin as the only protein or the inorganic iron enriched ES-ERDF without insulin in the same way as in the ITES-ERDF containing insulin and transferrin.

EXAMPLE 3

(1) Measurement of Antibody Productivity

The HB8852 was seeded into a tissue culture flask, in the density of $5 \times 10^4$ cells/ml, in the ferrous sulfate enriched IES-ERDF, ES-ERDF, or the ERDF containing 10% FCS, and cultured for three days.

Then, IgG secreted into the supernatant of the culture was measured by ELISA (Immunochemistry, Vol. 8, pages 871–874, 1971).

(2) Result

Antibody Productivity by Hybridoma in Inorganic Iron Enriched Serum-Free Culture Medium The HB8852 was cultured in the ferrous sulfate enriched IES-ERDF, ferrous sulfate enriched ES-ERDF or ERDF containing 10% FCS for three days. The concentration of the antibody (IgG) secreted into the culture medium was measured by ELISA. Table 2 shows the result.

The ERDF containing the 10% FCS was used as the control. The antibody secretion therein was 0.216 (ug/$10^4$ cells).

On the contrary, the antibody productivity in the ferrous sulfate enriched IES-ERDF and ferrous sulfate enriched ES-ERDF was twice as much as the productivity in the ERDF containing 10% FCS.

TABLE 2

Antibody Productivity Yield By HB8852 in Serum-Free Culture Medium

| culture medium | Antibody (IgG) concentration (µg/ml) | cell density ($\times 10^4$ cells/ml) | yield per cell (µg/$10^4$ cells) |
| --- | --- | --- | --- |
| FeSO⁴ enriched IES-ERDF | 20.0 | 37.8 | 0.529 |
| FeSO₄ enriched ES-ERDF | 15.0 | 27.3 | 0.549 |
| 10% FCS added ERDF | 14.0 | 64.8 | 0.216 |

EXAMPLE 4

(1) Culture of hybridoma HB8852

The hybridoma HB 8852 was suspended at a cell density of $5 \times 10^4$ cells/ml in the ES-ERDF culture medium having therein 80 μM of ferrous sulfate and in the ES-RPMI 1640 having therein 80 μM of ferrous sulfate respectively and cultured for 6 days.

(2) Results

Figure 5:
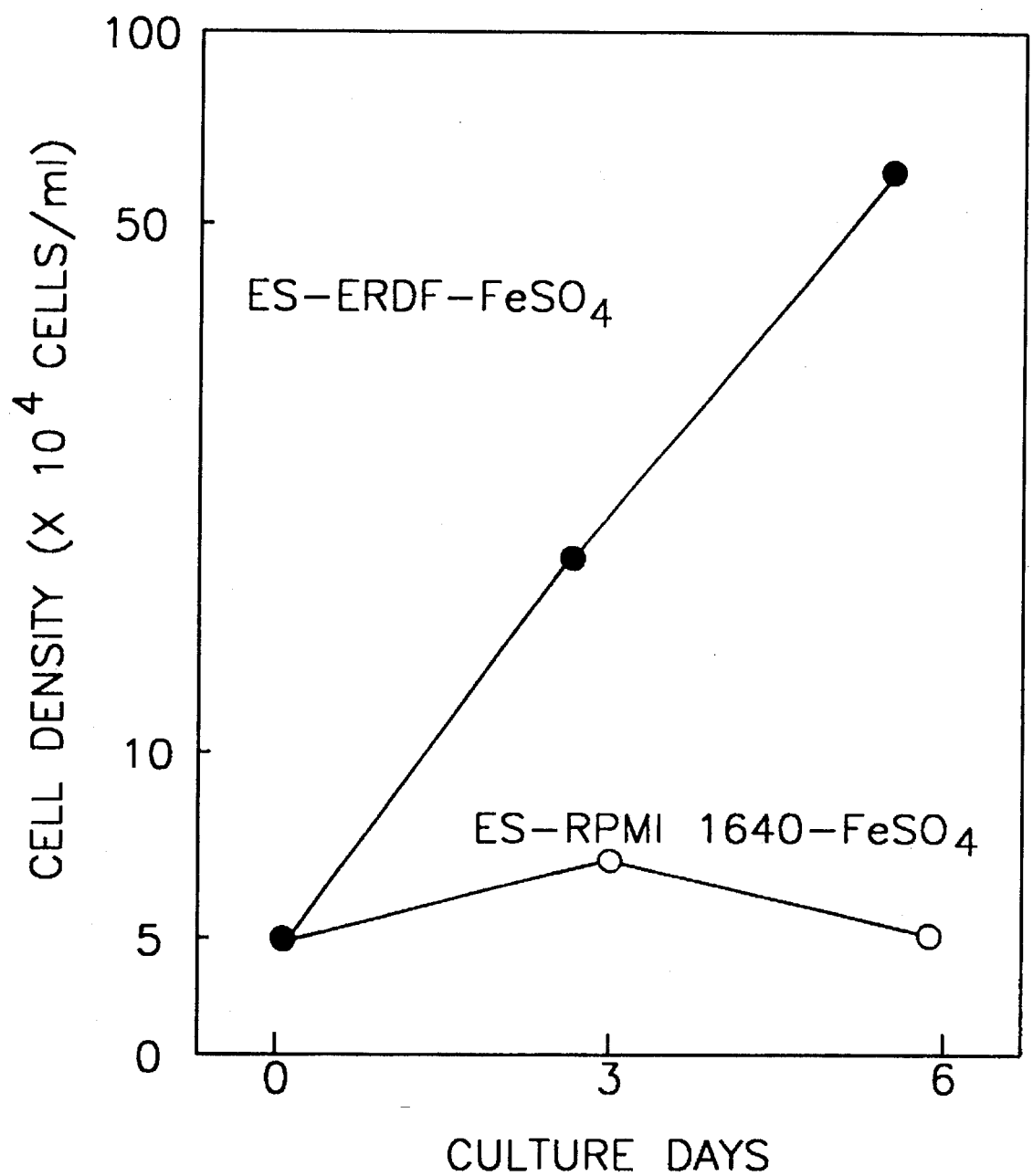
FIG. 5 shows a comparison of hybridoma cultured in ES-ERDF and ES-RPMI 1640, each containing ferrous sulfate.

The results are shown in FIG. 5.

When the cells were cultured in the above ES-ERDF-$FeSO_4$, the cells grew well. The cell density after 6 days from the first day of the culture reached to $60 \times 10^4$ cells/ml. Comparing with this result, when the cell was cultured in the above ES-RPMI 1640-$FeSO_4$ the, cell did not grow and the cell density at 6 days from the culture remained almost unchanged.

We claim:

1. A serum free basal synthetic culture medium solely for culturing hybridoma HB-8852, said medium consisting essentially of a mixture of ethanolamine, sodium selenite, RPMI 1640, Dulbecco's Modified Minimum Essential Medium and Ham's F12 (ES-ERDF), and containing at least one inorganic iron compound selected from the group consisting of ferrous sulfate, ferric nitrate and ferrous chloride, and wherein the concentration of the inorganic iron compound is about 80 μM of said basal synthetic culture medium.

2. The culture medium of claim 1 wherein the inorganic iron compound is ferrous sulfate 3. The culture medium of claim 1 wherein the inorganic iron compound is ferric nitrate.

4. The culture medium of claim 1 wherein the inorganic iron compound is ferrous chloride.

5. A method for culturing hybridoma HB-8852 which comprises culturing the hybridoma in a serum free ES-ERDF basal synthetic culture medium, said medium consisting essentially of a mixture of ethanolamine, sodium selenite, RPMI 1640, Dulbecco's Modified Minimum Essential Medium and Ham's F12 (ES-ERDF), and containing at least one inorganic iron compound selected from the group consisting of ferrous sulfate, ferric nitrate and ferrous chloride, and wherein the concentration of the inorganic iron compound is about 80 μM of said basal synthetic culture medium.

6. The method of claim 5 wherein the inorganic iron compound is ferrous sulfate.

7. The method of claim 5 wherein the inorganic iron compound is ferric nitrate.

8. The method of claim 5 wherein the inorganic iron compound is ferrous chloride.

* * * * *